United States Patent
Morgan et al.

(10) Patent No.: US 6,374,137 B1
(45) Date of Patent: Apr. 16, 2002

(54) METHOD AND APPARATUS FOR REDUCING DEFIBRILLATION ENERGY

(76) Inventors: Carlton B. Morgan, 4143 Palomino Dr. NE., Bainbridge Island, WA (US) 98110; Bradford E. Gliner, 4368 230th Way SE., Issaquah, WA (US) 98029; Dawn Jorgenson, 2512 Crestmont Pl. W., Seattle, WA (US) 98199; Kent W. Leyde, 2036 223rd Pl. NE., Redmond, WA (US) 98053

( * ) Notice: Subject to any disclaimer, the term of this patent is extended or adjusted under 35 U.S.C. 154(b) by 0 days.

(21) Appl. No.: 09/417,269

(22) Filed: Oct. 13, 1999

Related U.S. Application Data

(60) Division of application No. 09/113,803, filed on Jul. 9, 1998, now Pat. No. 6,134,468, and a continuation-in-part of application No. 08/775,827, filed on Dec. 31, 1996, now abandoned.

(51) Int. Cl.[7] ................................................. A61N 1/39
(52) U.S. Cl. ......................................................... 607/5
(58) Field of Search .............................. 607/1, 2, 5–8, 607/10, 143, 145, 148

(56) References Cited

U.S. PATENT DOCUMENTS

| | | | |
|---|---|---|---|
| 4,566,457 A | | 1/1986 | Stemple |
| 4,628,935 A | | 12/1986 | Jones et al. |
| 4,705,044 A | * | 11/1987 | Deluhery et al. ............ 607/142 |
| 4,823,796 A | * | 4/1989 | Benson ........................... 607/5 |
| 4,850,356 A | * | 7/1989 | Heath ............................. 607/5 |
| 5,593,427 A | | 1/1997 | Gliner et al. |
| 5,674,253 A | | 10/1997 | Adams et al. |
| 5,713,927 A | | 2/1998 | Hampele et al. |
| 6,101,413 A | * | 8/2000 | Olson et al. .................... 607/5 |
| 6,125,298 A | * | 9/2000 | Olson et al. .................... 607/5 |

OTHER PUBLICATIONS

Quan, et al. "Transcutaneous cardiac pacing in the treatment of out–of hospital pediatric cardiac arrest cases" Annals of Emergency Med. 21 (8):905–909 (1992).

Mogayzel, et al. "Out–of–hospital ventricular fibrillation in children and adolescents: Causes and outcomes" Annals of Emergency Medicine 25 (4): 484–491 (1995).

Zaritsky, et al. "Recommended guidelines for uniform reporting of pediatric advanced life support: the peduatric Utstein style" Pediatrics 904(4): 765–779 (1995).

Atkins et al. "Pediatric defibrillation: Current flow is improving by using 'Adult' electrode paddles" Pediatrics 94(1): 90–93 (1994).

Samson, et al. "Optimal size of self–adhesive preapplied electrode pads in pediatric defibrillation" The American Journal of Cardiology 75:544–545 (1995).

Quan, et al. (Letter to the Editor) "Ventricular fibrillation in pediatric cardiac arrest" Annals of Emergency Medicine 26(5):658–659 (1995).

* cited by examiner

*Primary Examiner*—George R. Evanisko

(57) ABSTRACT

An energy reduction unit is removably connectable to an external defibrillator to reduce the defibrillation energy delivered by the defibrillator to a patient. Use of the energy reduction unit is particularly suited to defibrillating pediatric patients (infants and children under 8) with an automatic or semi-automatic external defibrillator (AED). In one embodiment, the energy reduction unit includes an attenuator which partially dissipates energy produced by the AED. The attenuator is advantageously designed to present an impedance to the AED which, when connected to the patient, is approximately equal to the patient's impedance. The energy reduction unit may include a presence-detect function which enables the defibrillator to modify analysis of ECG signals to account for differences heart rhythms of pediatric and adult patients. In a second embodiment, the energy reduction unit includes an energy control modifier circuit which affects the charging operations performed internal to the AED. Other than being attached to the defibrillation equipment, the energy reduction unit does not otherwise change how an operator uses the equipment.

3 Claims, 9 Drawing Sheets

METHOD AND APPARATUS FOR REDUCING DEFIBRILLATION ENERGY

CROSS REFERENCE TO RELATED APPLICATION(S)

This is a divisional of application Ser. No. 09/113,803 filed on Jul. 9, 1998 now U.S. Pat. No. 6,134,468.

CONTINUING DATA

This application is a continuation-in-part of application Ser. No. 08/775,827 filed Dec. 31, 1996, now abandoned, for "Method and Apparatus for Reducing Defibrillation Energy."

TECHNICAL FIELD

This invention relates generally to a defibrillation method and apparatus, and more particularly to a method and apparatus for reducing the electrical energy delivered by an external defibrillator. "Defibrillators" include manual defibrillators, semi-automatic defibrillators and automatic defibrillators. This invention also relates to a method and apparatus for dynamically changing the operation of a defibrillator when treating a pediatric patient.

BACKGROUND OF THE INVENTION

Sudden cardiac death is the leading cause of death in the United States. Most sudden cardiac death is caused by ventricular fibrillation ("VF"), in which the heart's muscle fibers contract without coordination, thereby interrupting normal blood flow to the body. The only known effective treatment for VF is electrical defibrillation, in which an electrical pulse is applied to the patient's heart. The electrical pulse must be delivered within a short time after onset of VF in order for the patient to have any reasonable chance of survival. Electrical fibrillation may also be used to treat shockable ventricular tachycardia ("VT"). Accordingly, defibrillation is the appropriate therapy for any shockable rhythm, i.e., VF or shockable VT.

One way of providing electrical defibrillation uses implantable defibrillators, which are surgically implanted in those patients having a high likelihood of experiencing VF. Implanted defibrillators typically monitor the patient's heart activity and automatically supply the requisite electrical defibrillation pulses to terminate VF. Implantable defibrillators are expensive, and are used in only a small fraction of the total population at risk for sudden cardiac death.

External defibrillators send electrical pulses to the patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators (referred to collectively as "AEDs") are becoming increasingly popular because they can be used by relatively inexperienced personnel. Such AEDs are also especially lightweight, compact, and portable. AEDs are described in U.S. Pat. No. 5,607,454 to Cameron et al. entitled "Electrotherapy Method and Apparatus" and PCT Publication No. WO 94/27674 entitled "Defibrillator with Self-Test Features", the specifications of which are incorporated herein.

AEDs provide a number of advantages, including the availability of external defibrillation at locations where external defibrillation is not regularly expected, and is likely to be performed quite infrequently, such as in residences, public buildings, businesses, personal vehicles, public transportation vehicles, etc. Although operators of AEDs can expect to use an AED only very occasionally, they must nevertheless perform quickly and accurately when called upon. For this reason, AEDs automate many of the steps associated with operating external defibrillation equipment, and the operation of AEDs is intended to be simple and intuitive: AEDs are designed to minimize the number of operator decisions required.

Because AEDs have primarily been designed to treat adult VF and shockable VT, AEDs are typically not recommended for treating pediatric patients. One reason is that pediatric VF is not well documented and understood. For example, the optimal energy required for defibrillating infants and children has not yet been established—although currently available information suggests a starting dose of 2 J/kg. Additionally, the criteria used to analyze adult VF would not necessarily be appropriate for pediatric VF because of physiological differences between adults and pediatric patients. Such differences include, for example, heart rate. Finally, the protocol recommended for treating a pediatric victim of sudden cardiac arrest is different than the protocol recommended for treating an adult largely because pediatric VF is typically associated with respiratory failure. (See, Chameides et al. (Eds.) "Pediatric Advanced Life Support" (1997–1999) American Heart Assn).

FIG. 1 is a functional block diagram depicting an AED 20 and an electrode unit 21. The electrode unit 21 includes defibrillation electrodes 22 which are connected to a connector 23 by electrode wires 25. In operation, an operator attaches the defibrillation electrodes 22 to a patient 24, and plugs the connector 23 of the electrode unit 21 into a connector 26 of the AED 20. The operator then turns on the AED 20, and ECG signals are gathered by the electrodes 22 and routed to an ECG amplifier 28 within the AED. An A/D converter 30 receives the analog output of the ECG amplifier 28, and provides corresponding digital samples to a microcomputer 32 for analysis. If the patient 24 is currently experiencing VF, the microcomputer 32 asserts a control signal to cause a high voltage charger 34 to transfer electrical energy from a low voltage source, such as a battery 36, to a high voltage energy storage device, such as a capacitor 38. In the case of semi-automatic AEDs, the operator is then prompted by the AED 20 to issue a shock command by depressing a shock control switch 39. In the case of fully automatic AEDs, the shock command is initiated by the microcomputer 32, and no shock control switch 39 is provided. In response to the shock command, the microcomputer operates a discharge switch 40 to deliver an electric shock to the patient 24 through the electrodes 22.

As mentioned above, the use of AEDs for pediatric patients generally has not been considered, primarily because of concerns with potential operator confusion and machine complexity. When defibrillating pediatric patients, the operator must know the appropriate energy dose to deliver, which is based on the pediatric patient's weight or age. In practical terms, this means that an AED must have the necessary circuitry to accurately produce at least two energy levels (adult and child). Because the AED cannot automatically detect the presence of a pediatric patient, the AED must provide the operator with a means, such as an energy selector switch, to choose the proper energy level. It is also necessary that the AED properly analyze VF in pediatric patient. This may require the AED to be informed, via an operator action, that a pediatric patient is present in order to appropriately modify the ECG analysis to account for the differences between heart rhythms of pediatric and adult patients. The need for an operator to select an appropriate energy level, and to indicate to the AED whether a pediatric or adult patient is present, complicates both the AED design and the operator decision making process each time the AED is used. Added complexity is of particular concern for first responder AEDs which are designed for infrequent use, and are typically used by persons whose primary occupation is not lifesaving (such as police officers or flight attendants). Concerns regarding the possible consequences of such complications have outweighed any expected benefits associated with the small utilization rate of AEDs for pediatric patients. Nevertheless, the inability to effectively treat an infant or child near death is difficult to accept.

What is needed is a simple and effective way of reducing the amount of energy delivered to a pediatric patient by an AED. Additionally, what is needed is a device that lowers the defibrillator energy delivered to a pediatric patient as well as enables the defibrillator to modify its behavior to more effectively treat a pediatric patient. Additionally, what is needed is a device that enables the ECG analysis capabilities to dynamically change when the pediatric energy reduction unit is in place. Finally, what is needed is a simple and effective way of reducing the amount of energy delivered to a pediatric patient by a traditional AED, but which allows a seamless hand-off to a manual defibrillator (or an AED with manual capabilities).

SUMMARY OF THE INVENTION

A method and apparatus is provided for reducing energy delivered by an external defibrillator to a child or infant patient. An energy reduction unit is removably connectable to the defibrillator. In one embodiment, the energy reduction unit includes an attenuator which partially dissipates energy produced by the defibrillator. The attenuator may be designed to present an impedance to the AED which, when connected to the patient, is a function of the patient's impedance. The energy reduction unit may also include a presence-detect function which enables the defibrillator to modify ECG signal analysis to account for differences between heart rhythms of pediatric and adult patients. Additionally, the energy reduction unit may also change the care procedures the defibrillator prompts the rescuer to follow. In a second embodiment, the energy reduction unit includes an energy control modifier circuit which affects the charging operations performed internal to the AED. Once an operator has determined that a pediatric patient falls below a selected measurement threshold level, the operator connects the energy reduction unit to the defibrillator. All other steps performed by the operator are identical to those steps performed when defibrillating an adult.

DETAILED DESCRIPTION OF THE INVENTION

In one embodiment, an energy reduction unit is described which is removably connectable to currently available AEDs and which provides the means for effectively treating pediatric patients with an AED, but without otherwise complicating AED design or operator interaction. The energy reduction unit reduces the amount of electrical energy delivered to a pediatric patient by an AED. As used herein, "pediatric" includes all children under the age of 8. Typically, "pediatric" is further divided into two sub-groups: "infant" (0–1 yr) and "child" (1–7 yr). In the following description, certain specific details are set forth in order to provide a thorough understanding of the preferred embodiment of the present invention. It will be clear, however, to one skilled in the art that the present invention may be practiced without these details. In other instances, well-known circuits have not been shown in detail in order not to unnecessarily obscure the description of the various embodiments of the invention. Also not presented in any detail are those well-known control signals and signal timing protocols associated with the internal operation of AEDs.

Figure 1:
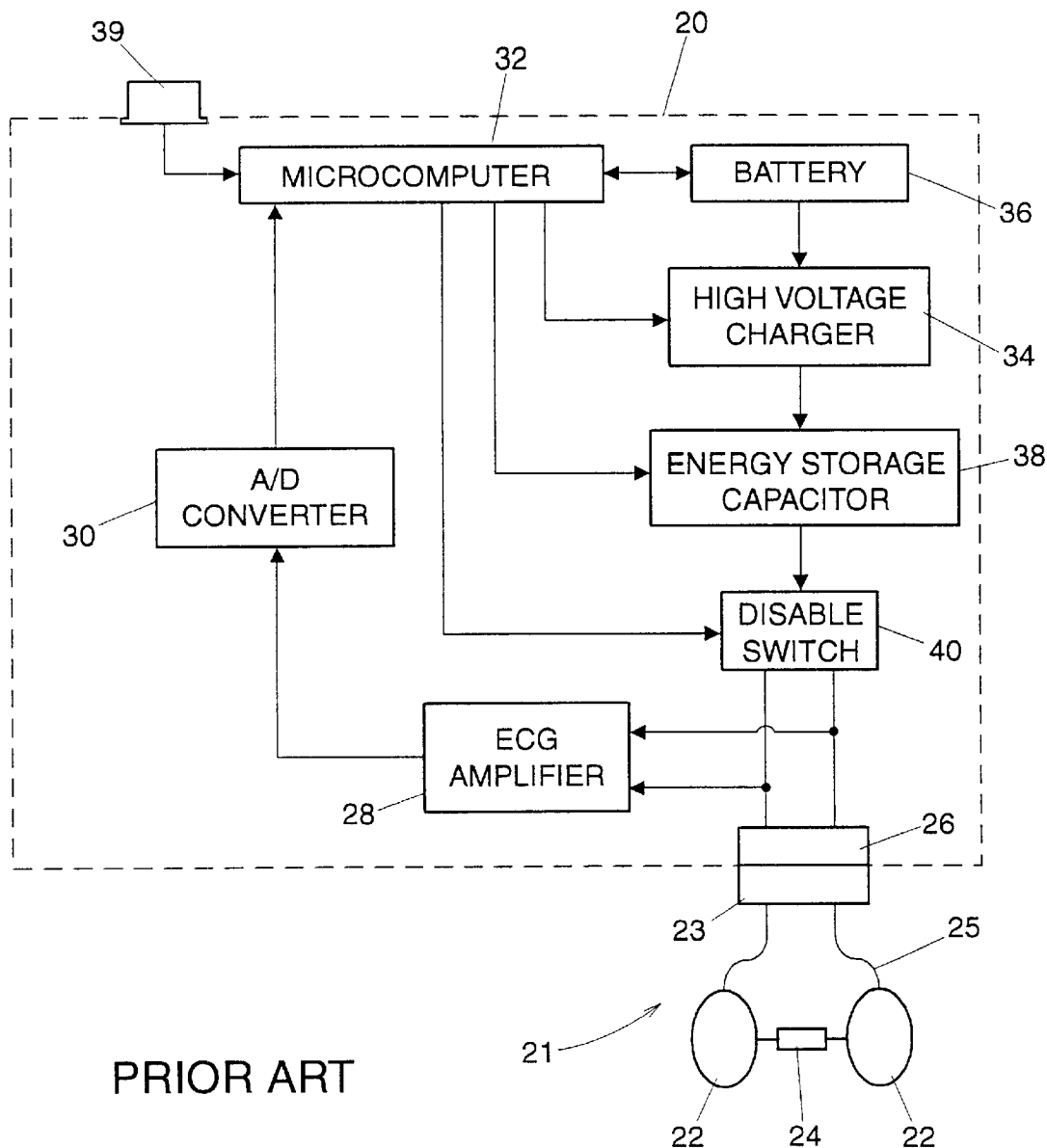
FIG. 1 is a functional block diagram depicting a prior art automatic or semi-automatic external defibrillator (AED).
Figure 2:
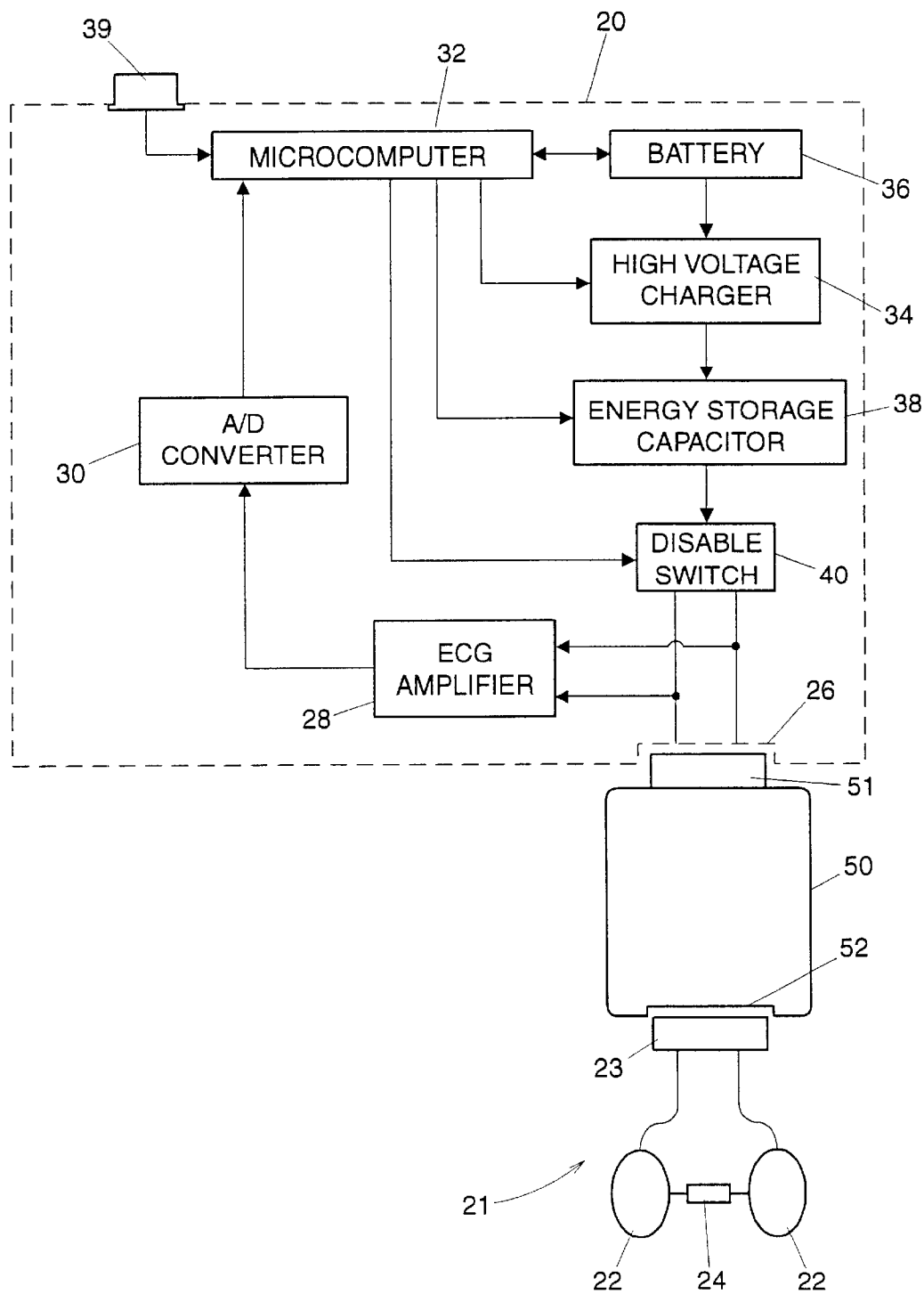
FIG. 2 is a functional block diagram depicting an energy reduction unit, according to the present invention, used in combination with the AED of FIG. 1.

Referring to FIG. 2, an energy reduction unit 50 is shown in combination with the AED 20 described above in connection with FIG. 1. The energy reduction unit 50 is removably connectable to the connector 26 of the AED 20, by virtue of having a connector 51 of the same configuration as the connector 23 of the electrode unit 21. The energy reduction unit 50 also includes a connector 52, of the same configuration as the connector 26 of the AED 20, to provide for connection to the connector 23 of the electrode unit 21. Although FIG. 2 depicts the energy reduction unit 50 used in combination with the electrode unit 21 ordinarily used on adults, those skilled in the art will appreciate that pediatric-specific electrodes (both "child" and "infant") may be used which are, for example, sized differently than adult electrodes. Also, while FIG. 2 depicts the energy reduction unit 50 as separate from and connectable to the electrode unit 21, those skilled in the art will appreciate that pediatric-specific electrode units may be designed which integrate one or more of the energy reduction unit features (described below) within the electrode unit itself.

Other than the simple placement of the energy reduction unit 50 between the AED 20 and the electrode unit 21, performing defibrillation for a pediatric patient 54 may be the same as the procedure for an adult patient 24, as outlined above in connection with FIG. 1. No additional operator procedure complexity or AED design complexity need be introduced.

When treating a pediatric patient with the energy reduction unit shown in FIG. 2, the rescuer connects the connector 23 of the electrode unit 21 to the energy reduction unit 50 and then connects the resulting combination to the AED 20. All other aspects of operating the AED remain the same. As a result, the only additional step taken by the rescuer is attaching the energy reduction unit 50. This additional step results in lower energy being delivered to the patient without unnecessarily complicating the procedure or increasing the cost of the defibrillator.

To appreciate some of the advantages achieved by use of the energy reduction unit 50 when defibrillating a pediatric patient, consider instead an AED designed to include an energy selector switch. In addition to increasing the complexity of the AED design, an operator of the AED would have to determine the appropriate setting of the energy selector switch each time the AED is used. In the event of operator error, an adult experiencing VF would then receive an inappropriately low energy defibrillation pulse, and the defibrillation procedure could be unsuccessful. Conversely, in the event of an operator error, a pediatric patient may receive an inappropriately high energy defibrillation pulse, with possible adverse consequences. Defibrillating a pediatric patient is unusual, and ideally it should be unnecessary to require an operator of an AED to consider the unusual case in every use of the instrument. In accordance with the present invention, the operator of an AED need only consider the steps associated with defibrillating a pediatric patient in the event that such an action is actually required. In the unusual case of defibrillating a pediatric patient, the operator performs a correspondingly unusual action— namely, connecting a pediatric-specific electrode unit and/or energy reduction unit to the AED.

Figure 3A:
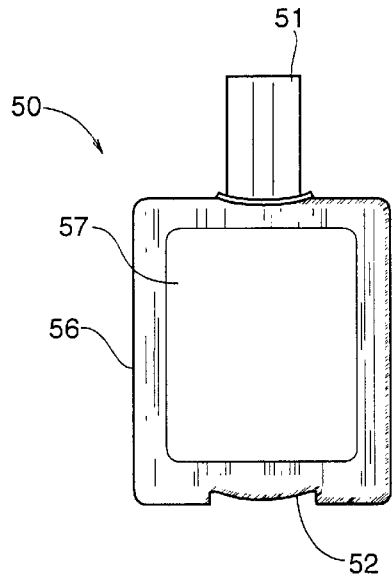
FIG. 3A is a plan view depicting a first electrical connector structure of the energy reduction unit of FIG. 2.
Figure 3B:
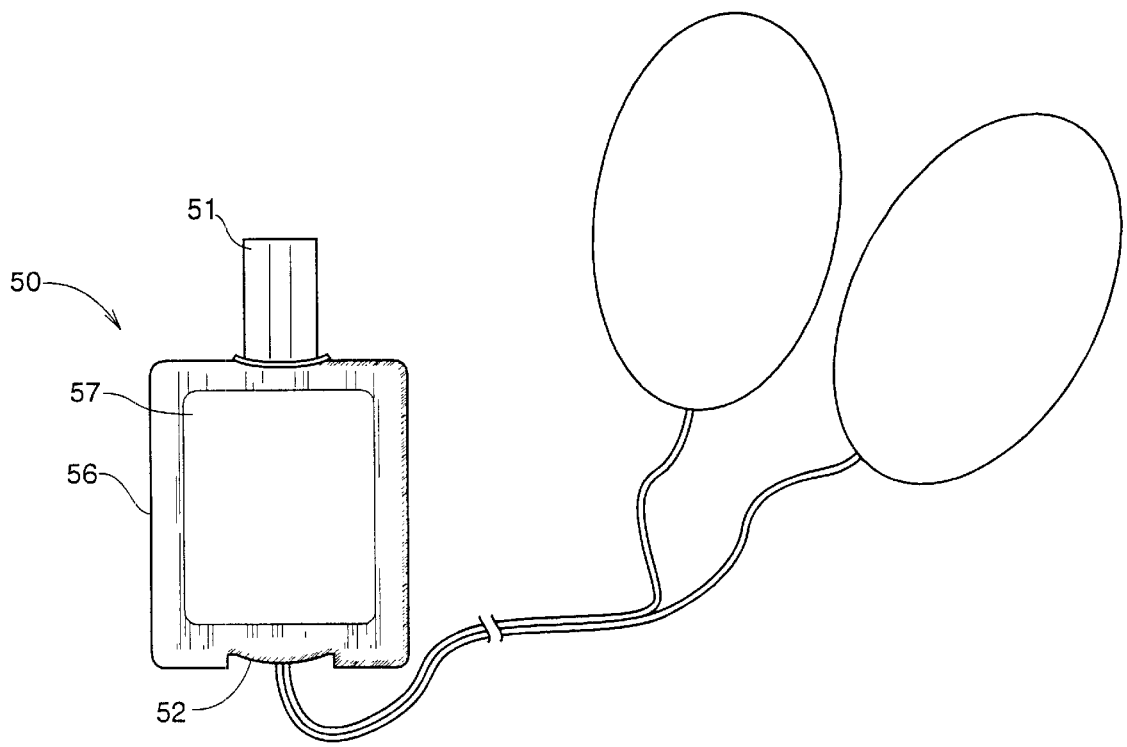
FIG. 3B is a plan view depicting an electrode system incorporating an energy reduction unit.
Figure 4:
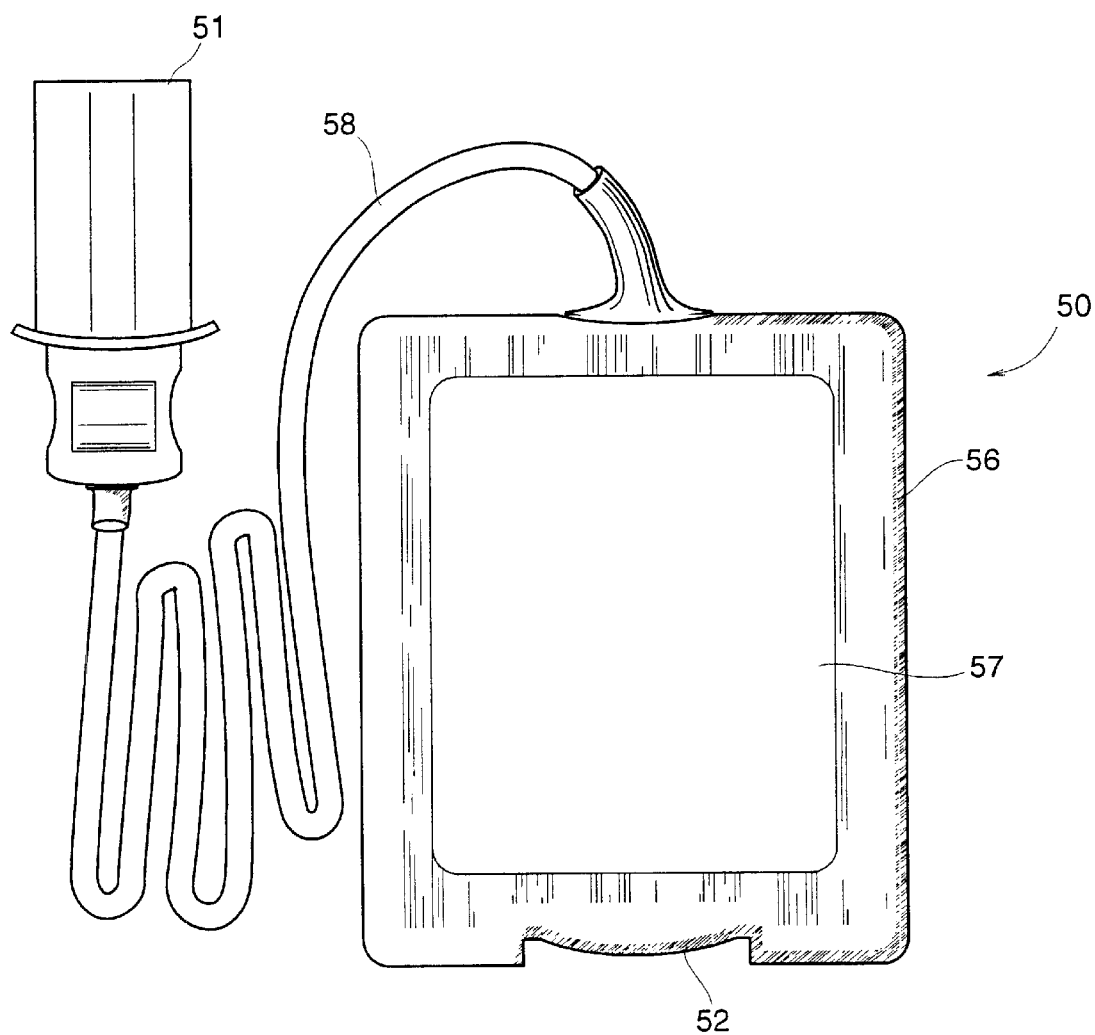
FIG. 4 is a plan view depicting a second electrical connector structure of the energy reduction unit of FIG. 2.

FIGS. 3A, 3B and 4 depict alternate connector/housing structures for the energy reduction unit 50. Each shows a similarly constructed circuit housing 56 with the connector 52 suitable for receiving the connector 23 of the electrode unit 21 (see FIG. 1). The circuit housing 56 has a flat configuration to permit easy storage, and to permit a large, graphical label 57 describing the proper use of the energy reduction unit 50. FIG. 3A shows the connector 51 of the energy reduction unit 50 mounted directly on the circuit housing 56. FIG. 3B shows an energy reduction electrode assembly which includes electrodes formed with an energy reduction unit 50. FIG. 4 shows the connector 51 of the energy reduction unit 50 connected to the circuitry within the circuit housing 56 via a cable 58 (which may be retractable, as desired). The length of the cable 58 is selected to correspond with the average height of a child weighing 25 kilograms (a conventional threshold value) or infant. Additionally, one cable length may be provided which contains markings to indicate the height for an infant and a child. In this way, an operator can quickly and easily determine whether the energy reduction unit 50 should be employed, or whether the pediatric patient should be defibrillated as an adult.

When treating a pediatric patient with the energy reduction unit shown in FIG. 3A, the rescuer connects the connector 23 of the electrode unit 21 (shown in FIG. 2) to the energy reduction unit 50 at connector 52 and then connects the resulting combination to the AED 20 (also shown in FIG. 2). All other aspects of operating the AED remain the same. As a result, the only additional step taken by the rescuer is attaching the energy reduction unit 50.

Alternatively, when treating a pediatric patient with the energy reduction unit shown in FIG. 3B, the rescuer connects the connector 51 of the electrode assembly to the AED 20 (shown in FIG. 2). All other aspects of operating the AED remain the same. As a result, no additional steps are required aside from selecting the appropriate electrodes (e.g., electrodes with an energy reduction unit or without).

When treating a pediatric patient with the energy reduction unit of FIG. 4, the rescuer uses the cable 58 as a gauge to measure the height of the patient. Two lengths, one for an infant and one for a child may be employed. Alternatively, one length may be used which provides an indication of the length of an infant and a child. If, for example, the height of the patient exceeds the cord length for an infant, then the rescuer knows that the child energy reduction unit 50 should be employed. If, however, the height of the patient exceeds the cord length for a child, then the rescuer knows that the standard adult electrodes should be used and the energy reduction unit is not required. All other aspects of operating the AED remain the same.

Figure 5:
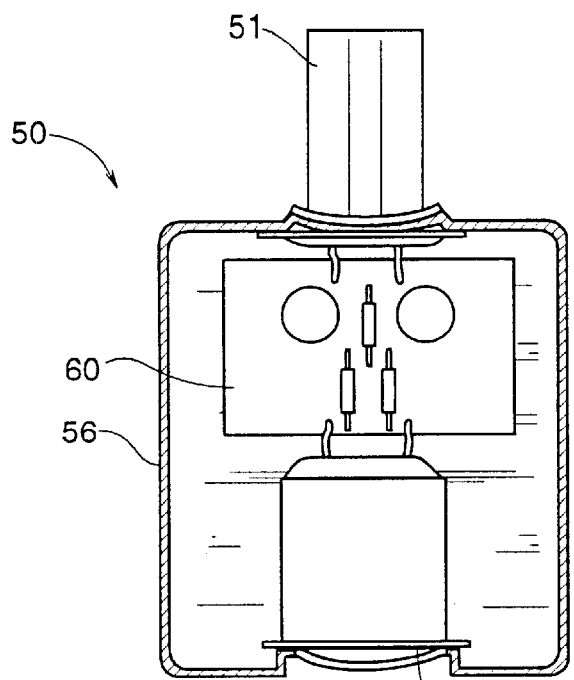
FIG. 5 is a functional block diagram depicting a first embodiment of the energy reduction unit of FIG. 2, and includes an attenuator.

FIG. 5 depicts a first embodiment of the energy reduction unit 50 and includes an attenuator 60. The attenuator 60 partially dissipates the energy produced by the AED 20 to provide a child-appropriate or infant-appropriate energy level at the electrodes 22. For example, a typical AED supplies a fixed output energy of not less than approximately 130 J, which is a suitable energy for adults. When used on a child, the attenuator 60 dissipates approximately 80 J of energy and delivers the remaining 50 J to the child patient— an appropriate dose for children up to 25 kilograms in weight. When used on an infant, the attenuator 60 dissipates 115 J of energy and delivers the remaining 25 J to the infant. For children over 25 kilograms, the energy reduction unit 50 is not employed and the adult energy level is delivered.

Figure 6A:
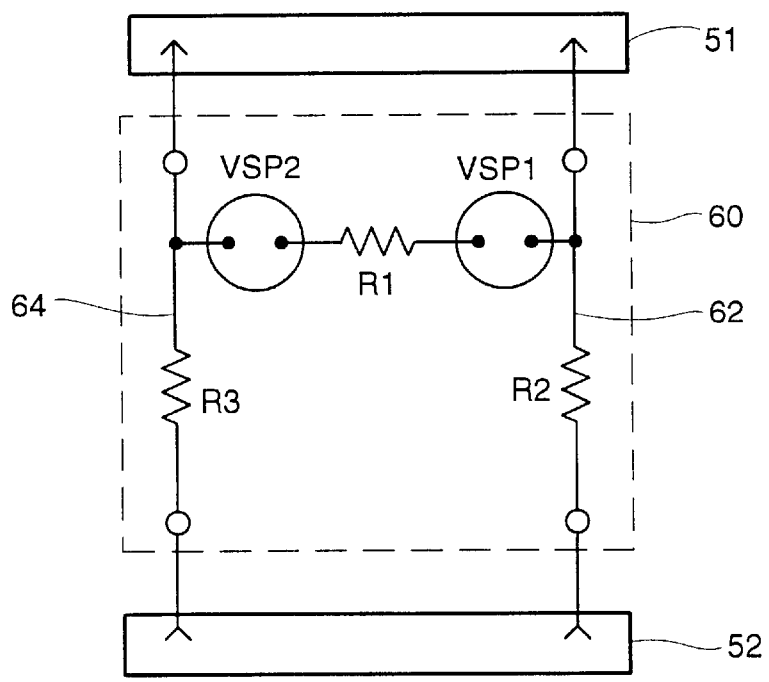
FIG. 6A is a schematic diagram depicting a preferred embodiment of the attenuator of FIG. 5.

FIG. 6A is a schematic diagram which depicts a first preferred embodiment of the attenuator 60. Included are first and second spark gaps $VSP_1$ and $VSP_2$ which are placed in series with a resistor $R_1$ between first and second signal lines 62, 64. The signal line 62 connects the connector 51 with the connector 52 and includes a resistor $R_2$. The signal line 64 also connects the connector 51 with the connector 52 and includes a resistor $R_3$. For purposes of minimizing common-to-differential mode conversion effects, $R_2$ and $R_3$ are shown as separate resistors, and are of equal value, but could also be combined into a single resistor in either of the signal lines 62, 64. Similarly, two spark gaps $VSP_1$ and $VSP_2$ are used to minimize the effects of common mode currents, but a single spark gap could suffice.

Normally, when a patient's ECG is being monitored and analyzed, the patient's equivalent circuit in series with the electrodes is a high impedance source of approximately 10 kΩ and 1 mV. When this signal is transmitted through the signal lines 62, 64, the spark gaps $VSP_1$ and $VSP_2$ are non-conducting and appear as an open circuit. The selected resistance values of resistors $R_2$ and $R_3$ are such as to have no appreciable effect on the high impedance ECG signal delivered from the patient to the ECG amplifier 28 within the AED 20 (see FIG. 2).

During defibrillation energy delivery, a high voltage is applied (e.g., approximately 1700V–2100V, more preferably 1800V). The equivalent patient circuit then appears to be of relatively low impedance, varying from approximately 50 to 125Ω with a mean of approximately 75Ω. During defibrillation, the high voltage pulse shorts spark gaps $VSP_1$ and $VSP_2$, thus introducing the resistor $R_1$ as a shunt resistance. Those skilled in the art will appreciate that the spark gaps $VSP_1$ and $VSP_2$ function as voltage-sensitive switches, such that a high applied voltage promotes conduction therethrough. This function can be accomplished by numerous other well-known means. For example, one or more diodes may be employed which become(s) forward biased when a high voltage is applied.

It is desirable that the equivalent circuit of the patient 54 (see FIG. 2) plus attenuator 60 present an impedance indicative of the patient's actual impedance. Also, it is desirable that, of the 130 J produced by the AED 20, approximately 50 J is delivered to the patient 54. The values of the resistors $R_1$, $R_2$, and $R_3$ are calculable accordingly. For a typical patient impedance of approximately 75Ω, the value of $R_1$ is approximately 220Ω and the values of $R_2$ and $R_3$ are each approximately 20Ω. For these resistance values, and given the typical range of patient impedances, the impedance presented to the AED 20 varies from approximately 60Ω to 100Ω. The impedance presented to the defibrillator through the energy reduction unit 50 is thus a function of the actual patient impedance. The energy delivered to the patient is relatively constant, varying only slightly in a range from approximately 50 to 60 Joules.

Figure 6B:
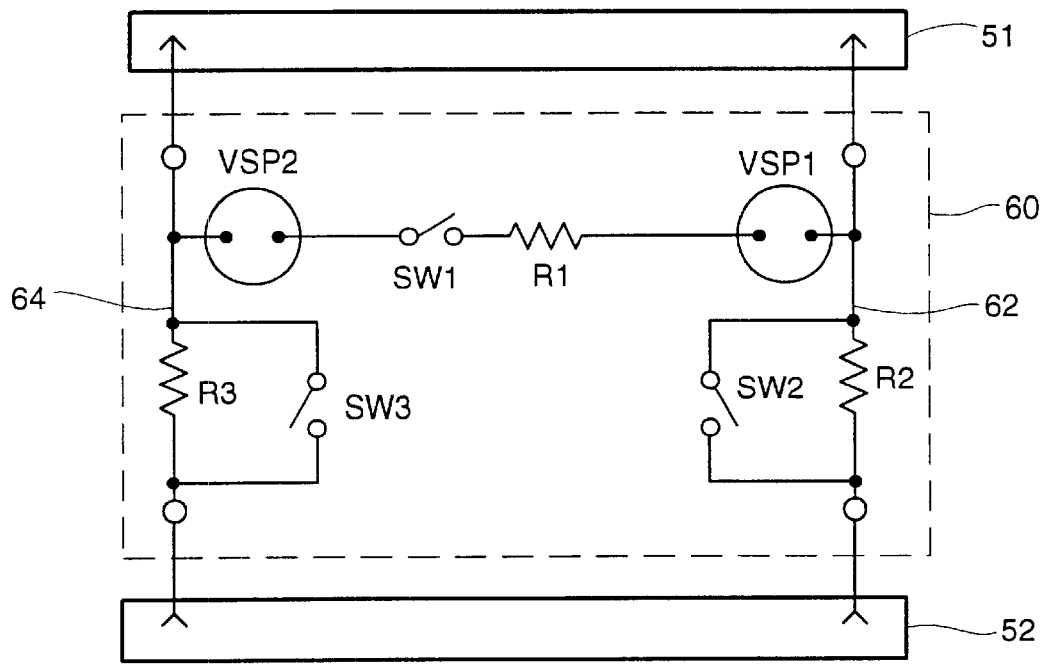
FIG. 6B is a schematic diagram depicting an alternate embodiment of the attenuator of FIG. 5.

FIG. 6B shows a second preferred embodiment of the schematic of the energy reduction unit wherein resistors $R_1$, $R_2$, and $R_3$ are controlled by switches, $SW_1$, $SW_2$, and $SW_3$, respectively. When switches $SW_1$ is open and switches $SW_2$ and $SW_3$ are closed, the energy is not attenuated. When switch $SW_1$ is closed and switches $SW_2$ and $SW_3$ are open, the energy is attenuated. When the energy reduction unit is initially attached, switch $SW_1$ is closed and switches $SW_2$ and $SW_3$ are open, thus allowing the energy to be attenuated. The switch positions are only reversed if, for example, the rescuer later activates a disarm button (provided externally on the energy reduction unit). The switch positions may also change as a result of connecting to an AED or manual defibrillator. For example, when a later arriving advanced cardiac life support ("ACLS") responder arrives (with a manual defibrillator or semi-automatic defibrillator with manual capabilities), the ACLS responder need only override the attenuation feature of the energy reduction unit 50. As a result, the ACLS responder can inactivate the energy reduction unit 50 without removing the unit or the electrode pads attached to the patient. Depending upon how the energy reduction unit 50 has been configured, the inactivation can occur automatically when the energy reduction unit 50 is connected to a defibrillator capable of manual settings, or manually, by the activation of a disarm button provided on the energy reduction unit 50. All other functions of the circuit are as described above with respect to FIG. 6A.

Figure 6C:
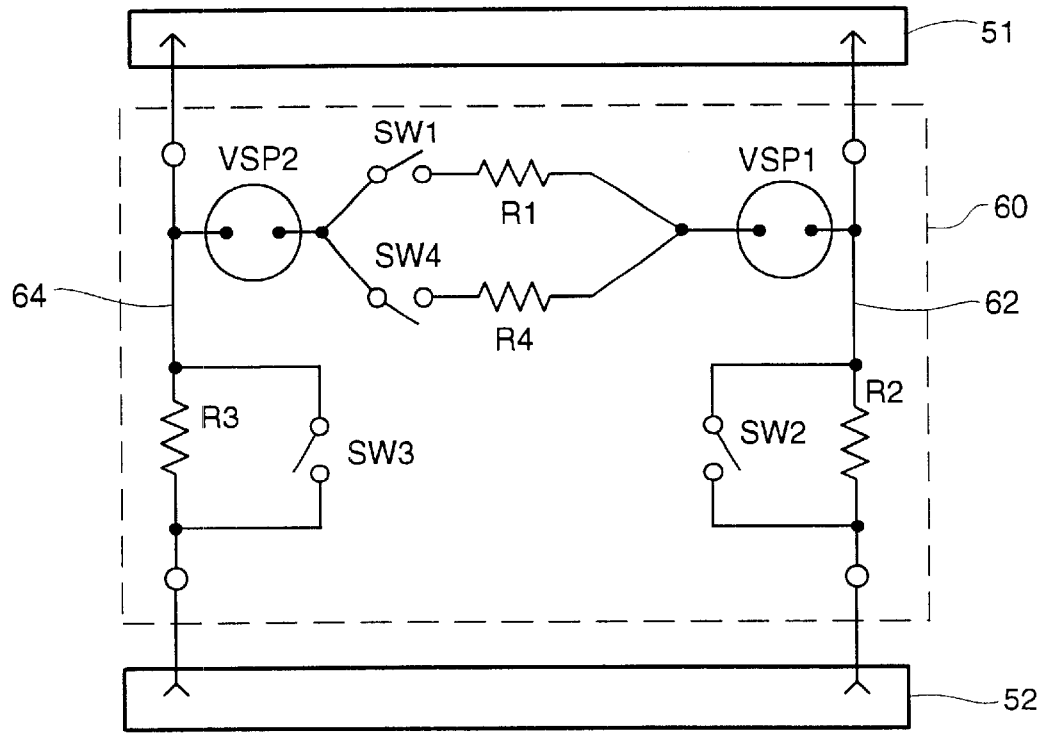
FIG. 6C is a schematic diagram depicting another alternate embodiment of the attenuator of FIG. 5.

FIG. 6C shows a third preferred embodiment of the energy reduction unit 50. Instead of a single resistor $R_1$ in series between the first and second spark gaps, $VSP_1$ and $VSP_2$, two resistors $R_1$ and $R_4$ are provided in parallel, where $R_1$ delivers infant energy and $R_4$ delivers child energy. Each resistor is controlled by a switch, shown as $SW_1$, $SW_2$, $SW_3$ and $SW_4$, respectively. Again, operation of the switches may be controlled by the operator or may occur automatically when the connector is attached to an AED or a manual defibrillator. When switches $SW_1$ and $SW_4$ are open and switches $SW_2$ and $SW_3$ are closed, energy is not attenuated. When switch $SW_1$ is closed, and switches $SW_2$, $SW_3$ and $SW_4$ are open, then resistor $R_1$ is in series between the spark gaps $VSP_1$ and $VSP_2$ resulting in the energy delivered by the defibrillator being attenuated and delivery of an energy appropriate for an infant. When switch $SW_4$ is closed, and switches $SW_1$, $SW_2$ and $SW_3$ are open, then resistor $R_4$ is in series between the spark gaps $VSP_1$ and $VSP_2$, resulting in an energy attenuation and delivery of an energy appropriate for a child. All other functions of the circuit are as described above with respect to FIG. 6A.

Figure 7:
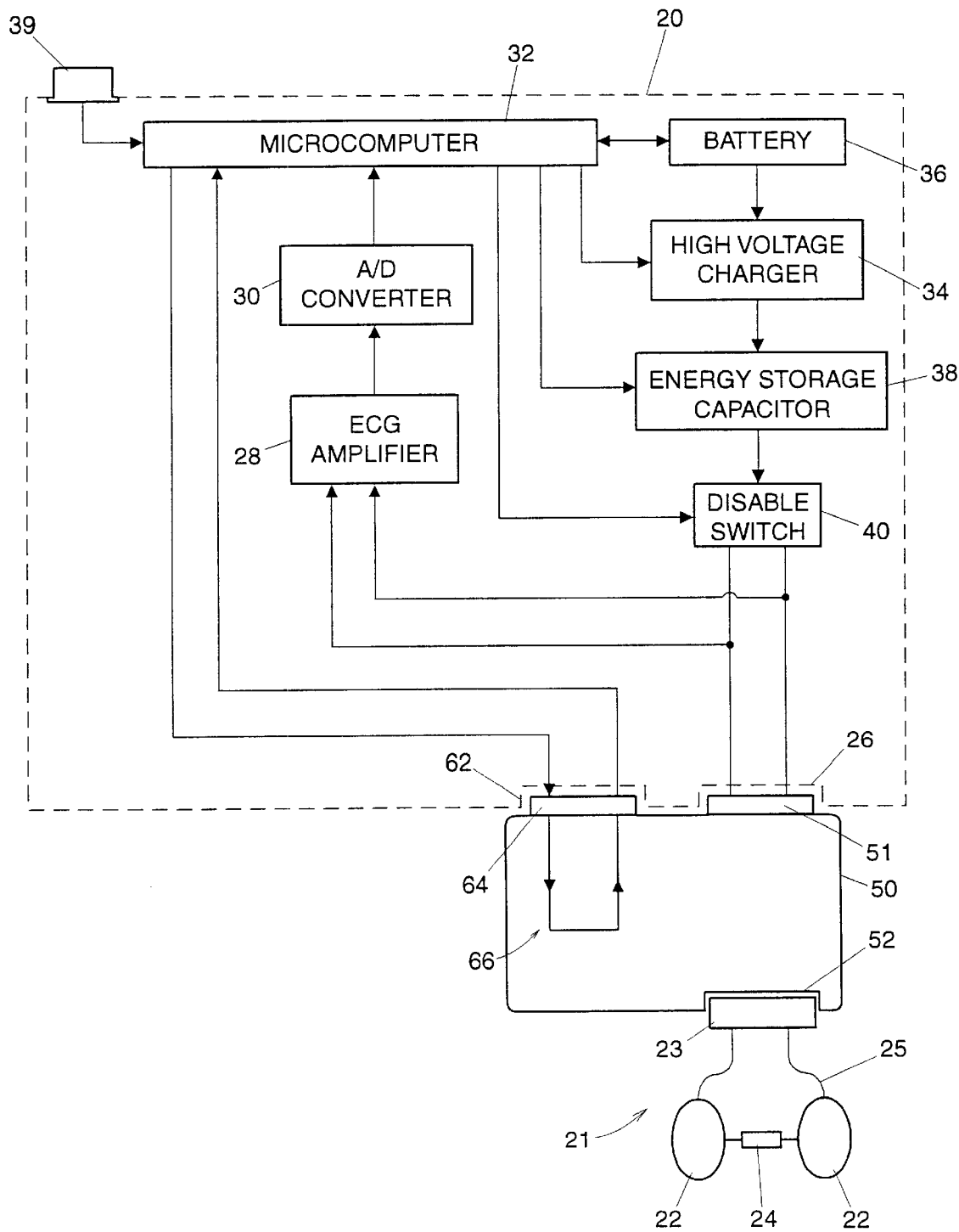
FIG. 7 is a functional block diagram depicting a second embodiment of the energy reduction unit of FIG. 2, and includes a presence-detect capability.

FIG. 7 depicts a second embodiment of the energy reduction unit 50, in which a presence-detect function has been added. This requires a relatively straightforward change to the design of the AED 20 to provide a presence-detect connector 62 and to provide presence-detect functionality to the microcomputer 32. Of course, the presence-detect connector 62 of the AED 20 can simply be additional pins or the equivalent integrated into the connector 26, as desired. The presence-detect connector 62 of the AED 20 receives a connector 64 of the energy reduction unit 50. Similarly, the connector 64 can be integrated as additional pins or equivalent into the connector 51 of the energy reduction unit 50.

In the example implementation depicted in FIG. 7, a simple signal loop 66 is provided which routes a presence-detect signal provided by the microcomputer 32 back to the microcomputer. In this way, the microcomputer 32 is informed of the presence of the energy reduction unit 50. Accordingly, the microcomputer 32 can modify analysis of the patient's ECG, to appropriately account for differences between the heart rhythms of pediatric and adult patients. The microcomputer 32 may also change the protocol followed and voice prompts presented to the rescuer in response to the appearance of the energy reduction unit 50.

In another embodiment of the signal loop 66 can route a different presence-detect signal for infant and child patients, thus allowing the defibrillator to further define the ECG analysis, voice prompts or protocol.

Where the presence detect circuit is incorporated into the electrodes, a separate circuit can be provided for each electrode type (e.g., adult, child or infant). By integrally forming the presence detect circuit with the electrodes, each electrode type can actively be identified by the defibrillator.

Those skilled in the art will appreciate that a presence-detect function can be provided by transmitting any of a wide variety of signals from the energy reduction unit 50 to the AED 20. For example, an optical or other electromagnetic signal can be used. Additionally, a mechanical signal can provide the presence-detect function, such as a portion of the connector 64 extending within the AED 20 to mechanically trip a switch. Finally an ID chip may be provided that communicates with the defibrillator to identify the electrode type or the presence and type of energy reduction unit.

In addition to signaling to the microcomputer 32 that ECG analysis must be modified, the presence-detect function may itself signal to the microcomputer 32 that a reduced energy delivery is required. In this way, the energy reduction unit 50 need not include the attenuator 60 (see FIG. 5) or other energy reducing circuitry—the reduction of energy delivery instead being accomplished by circuitry within the AED 20 itself. No increased operator complexity results from such an implementation, but a more complicated (and correspondingly more expensive) AED unit is required. An advantage of this embodiment is that the defibrillator can, in addition to lowering energy, also change the patient ECG analysis as well as the voice prompts and treatment protocol recommended by the defibrillator.

Figure 8:
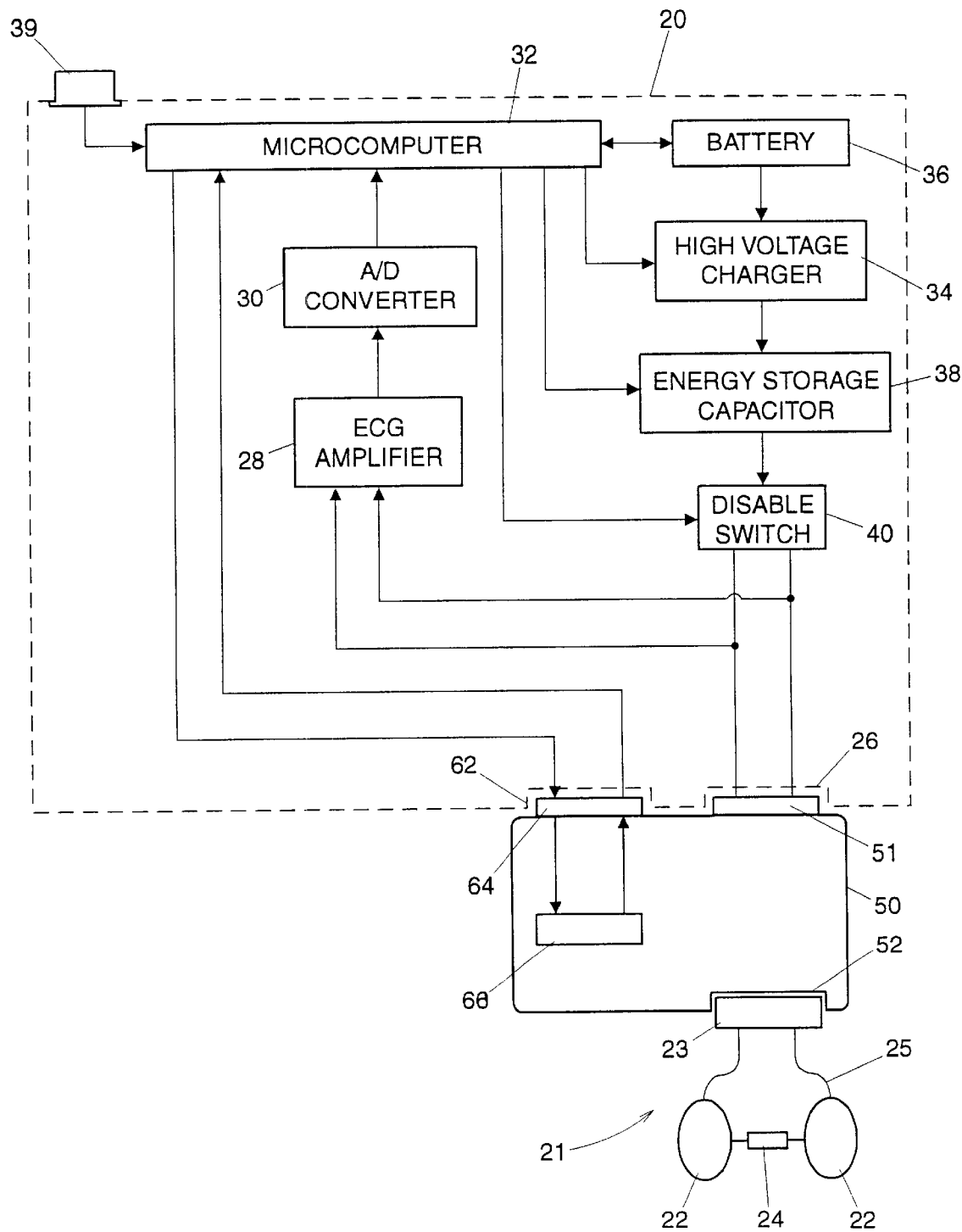
FIG. 8 is a functional block diagram depicting a third embodiment of the energy reduction unit of FIG. 2, and includes an energy control modifier.

FIG. 8 is a functional block diagram which depicts a third embodiment of the energy reduction unit 50. In this case, no dissipation or other attenuation of energy is accomplished internal to the energy reduction unit 50. Instead, an energy control modifier circuit 68 causes the high voltage charger 34 to cease charging the capacitor 40 at a lower voltage than when the energy control modifier circuit 68 is not present. The energy control modifier circuit 68 could include a comparator circuit or a resistor network and appropriate sensors, as will be clear to those skilled in the art. This embodiment is particularly suited to AEDs in which the operations of the high voltage charger 34 are not directly sensed and controlled by the microcomputer 32. Alternatively, the energy control modifier circuit 68 could assert a control signal to the microcomputer 32 or other circuitry within the AED 20 to effect a change of energy storage operations within the AED.

Additionally, the energy reduction unit 50 can contain program memory usable by the AED to appropriately modify the patient treatment protocol. For example, circuitry block 68 may contain read-only memory that is readable by microcomputer 32 when the energy reduction unit 50 is attached to the defibrillator. In use, the microcomputer 32 would follow instructions provided by memory in circuitry block 68 in order to follow a treatment protocol other than the default program of AED 20. This has the advantage of allowing the AED's protocol of operator interactions, voice prompts, delivered treatments, ECG analysis, and other factors to be modified when an energy reduction unit is connected to the AED. Thus, as treatment evolves (for example, a new recommended protocol for treating pediatric cardiac arrest victims), the AED owner can receive the benefits of upgraded treatments automatically by obtaining relatively inexpensive accessory modules.

Figure 9:
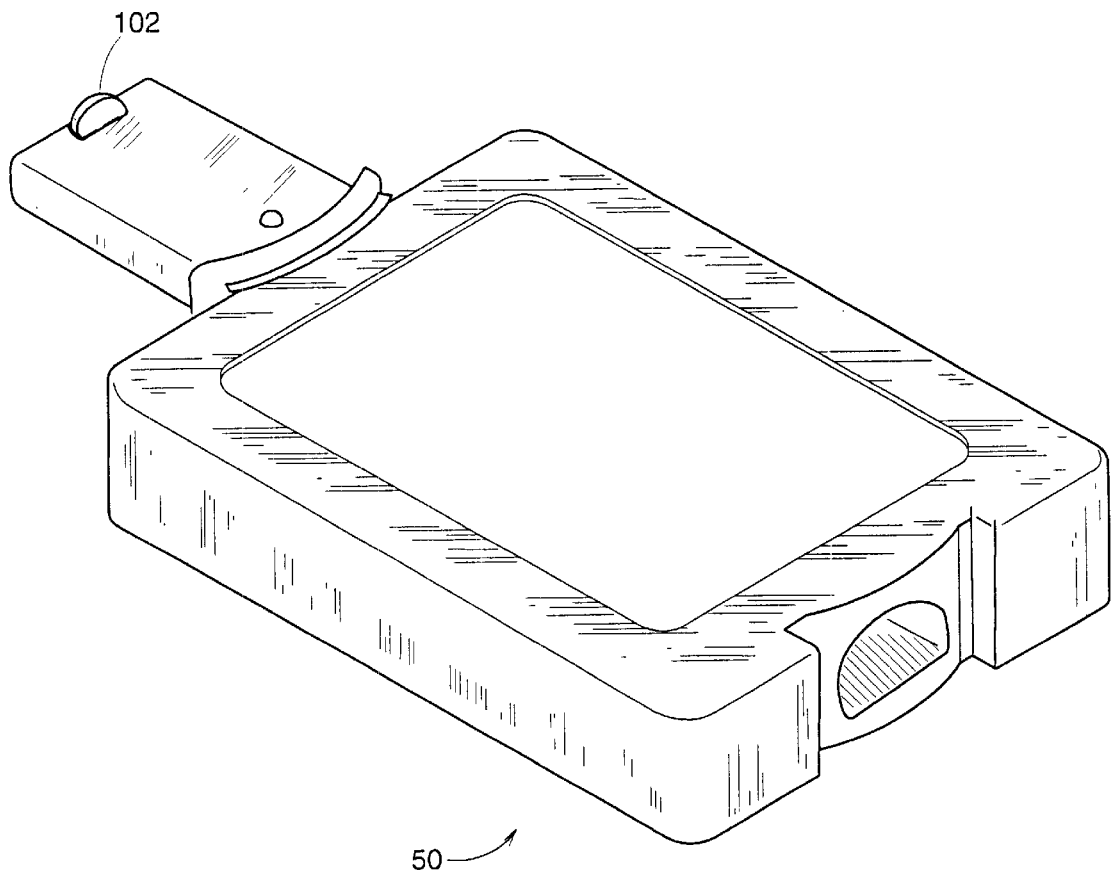
FIG. 9 is a perspective view of an alternate embodiment of the energy reduction unit shown in FIGS. 3 and 4.

FIG. 9 depicts a removable electrical connector 50, similar to the connector 50 shown in FIG. 3, except that it additionally provides a removable projection 102 on the connector 50. The removable projection 102 does not impede the ability of the connector 50 from being used with an AED. However, the removable projection 102 does prevent the connector and associated electrodes from attaching to a manual defibrillator, or an AED with manual capabilities without first removing the projection 102.

The operation of the energy reduction unit of FIG. 9 is substantially the same as the operation described with respect FIGS. 3 and 4. The advantage of the energy reduction unit of FIG. 9 is the removable projection 102. When a pediatric victim of sudden cardiac arrest is treated by a first responder using an AED which has been adapted to include the energy reduction unit, the AED delivers less energy to the pediatric patient as a result of the energy reduction unit. A later arriving ACLS responder (such as a second tier responder) will likely have either a manual defibrillator or an AED with manual capabilities. Since manual defibrillators can be set to deliver, for example, less energy, it would not be desirable to allow a pair of electrode pads with an energy reduction unit to be attached to a manual defibrillator because the manual defibrillator may be set to deliver the correct pediatric energy, but that energy would then be reduced by the energy reduction unit, thereby resulting in an ineffective shock. By providing a removable projection, the ACLS responder is alerted to the fact that the energy reduction unit was in place and could either remove the projection and deliver adult energy (knowing it would be reduced) or remove the energy reduction unit and deliver a reduced amount of energy.

The function and interconnection of a number of circuits are described above. These circuits are known in the art, and one skilled in the art would be able to use such circuits in the described combination to practice the present invention. The internal details of these particular circuits are not part of, nor critical to, the invention, and a detailed description of the internal circuit operation need not be provided.

While certain embodiments of the invention have been described for purposes of illustration, various modifications may be made without deviating from the spirit and scope of the invention. For example, the use of the energy reduction unit 50 has been described in connection with automatic and semi-automatic external defibrillators. However, the present invention can be advantageously used with a wide variety of external defibrillation equipment. Also, a particular attenuator configuration has been described in detail in connection with FIGS. 5 and 6. However, those skilled in the art will understand that a wide variety of circuits may be employed which partially dissipate the energy produced by a defibrillator, while presenting an impedance to the defibrillator which is a function of the patient impedance. Further, connector structures have been depicted schematically and described generally. Those skilled in the art will understand that any of numerous connector types may be used. Indeed, numerous variations are well within the scope of this invention. Accordingly, the invention is not limited except as by the appended claims.

What is claimed is:

1. A method of treating ventricular fibrillation in a pediatric patient with an electrical defibrillator calibrated for adults, the method comprising the steps of:

determining whether the pediatric patient is below a selected measurement threshold level, wherein the determining comprises comparing a linear dimension measurement of the pediatric patient to a corresponding linear dimension of the energy reduction unit;

if the pediatric patient is below the selected measurement threshold level, connecting an energy reduction unit to the electrical defibrillator, wherein the energy reduction unit automatically reduces the amount of energy delivered; and delivering defibrillation energy to the pediatric patient.

2. The method of claim 1 wherein the step of comparing a linear dimension measurement of the pediatric patient to a corresponding linear dimension of the energy reduction unit includes the step of comparing the height of the pediatric patient to the length of a cable included in the energy reduction unit.

3. A method of treating ventricular fibrillation in a patient by delivering defibrillation energy produced by a defibrillator to the patient, the method comprising the steps of:

determining whether the defibrillation energy delivered to the patient should be modified; and if the electrical defibrillation delivered to the patient should be modified, modifying the defibrillation energy delivered to the patient by connecting an energy modifier to the defibrillator which automatically reduces the amount of energy delivered, wherein modifying the defibrillation energy comprises modifying energy storage operations of the defibrillator by providing a mechanical signal from the energy modifier to the defibrillator.

\* \* \* \* \*